(12) United States Patent
Wang et al.

(10) Patent No.: US 8,083,951 B2
(45) Date of Patent: Dec. 27, 2011

(54) METHOD FOR PURIFYING QUENCH WATER AND SCRUBBING WATER FROM MTO BY MINI-HYDROCYCLONE AND APPARATUS USED FOR SAME

(75) Inventors: Hualin Wang, Shanghai (CN); Yanhong Zhang, Shanghai (CN); Qiang Yang, Shanghai (CN); Ji Ma, Shanghai (CN); Zhishan Bai, Shanghai (CN); Yu Liu, Henan (CN); Longhu Liang, Henan (CN); Lei Shi, Henan (CN); Jie Zhang, Henan (CN)

(73) Assignees: East China University of Science and Technology, Shanghai (CN); Luoyang Petrochemical Engineering Corporation (LPEC) Sinopec, Luoyang (CN)

( * ) Notice: Subject to any disclaimer, the term of this patent is extended or adjusted under 35 U.S.C. 154(b) by 271 days.

(21) Appl. No.: 12/427,578

(22) Filed: Apr. 21, 2009

(65) Prior Publication Data

US 2010/0059456 A1    Mar. 11, 2010

(30) Foreign Application Priority Data

Sep. 10, 2008  (CN) .......................... 2008 1 0042715
Sep. 10, 2008  (CN) .......................... 2008 1 0042716

(51) Int. Cl.
*C07C 1/00* (2006.01)
*C07C 7/00* (2006.01)
*B01D 21/26* (2006.01)

(52) U.S. Cl. ........ 210/774; 210/788; 210/805; 210/806; 210/195.1; 210/512.2; 585/639; 585/640; 585/809

(58) Field of Classification Search .................. 210/774, 210/788, 805, 806, 195.1, 512.2; 585/639, 585/640, 809
See application file for complete search history.

(56) References Cited

U.S. PATENT DOCUMENTS

| | | | |
|---|---|---|---|
| 5,744,680 A | 4/1998 | Mulvaney, III et al. | |
| 6,166,282 A | 12/2000 | Miller | |
| 6,870,072 B2 | 3/2005 | Lumgair et al. | |
| 7,119,241 B2 * | 10/2006 | Beech et al. .................. | 585/640 |
| 7,329,790 B2 | 2/2008 | Bjorklund et al. | |
| 2005/0234281 A1 | 10/2005 | Bjorklund et al. | |

FOREIGN PATENT DOCUMENTS

CN   1942558   4/2007

* cited by examiner

*Primary Examiner* — David A Reifsnyder
(74) *Attorney, Agent, or Firm* — Hamre, Schumann, Mueller & Larson, P.C.

(57) ABSTRACT

The invention provides a method for purifying MTO quench water and scrubbing water via mini-hydrocyclone separation, comprising: removing the entrapped catalyst particles from the MTO quench water via mini-hydrocyclone separation; cooling the quench water purified by mini-hydrocyclone separation so as to effect the recycling of water; removing the entrapped catalyst particles from the MTO quench water to be stripped via mini-hydrocyclone separation, so as to reduce the deposition of the catalyst particles within the stripping tower; removing the entrapped catalyst particles from the MTO scrubbing water via mini-hydrocyclone separation; and cooling the scrubbing water purified via mini-hydrocyclone separation so as to effect the recycling of water. The invention also provides an apparatus for purifying MTO quench water and scrubbing water via mini-hydrocyclone separation.

19 Claims, 3 Drawing Sheets

METHOD FOR PURIFYING QUENCH WATER AND SCRUBBING WATER FROM MTO BY MINI-HYDROCYCLONE AND APPARATUS USED FOR SAME

CROSS-REFERENCE TO RELATED APPLICATIONS

This application claims priority to Chinese Patent Application No. 200810042716.2, filed on Sep. 10, 2008, and Chinese Patent Application No. 200810042715.8, filed on Sep. 10, 2008, the entire contents of both of which are incorporated herein by reference.

TECHNICAL FIELD

The invention relates to the field of coal conversion technology, particularly to a method for removing the small amount of catalyst particles left in the quench water and the scrubbing water from the process of MTO using mini-hydrocyclone separators, which is suitable for solid-liquid heterogeneous separation processes including the processes of treating the quench water and scrubbing water from MTO. Specifically, the invention provides a method for removing solids from MTO quench water and scrubbing water via mini-hydrocyclone separation.

TECHNICAL BACKGROUND

The main principle of MTO (methanol-to-olefins process), lies in that methanol is first produced from synthetic gas which is derived from coal used as the starting material, and then the methanol is converted to lower olefins (which mainly include ethylene and propylene) which are used for other chemicals and industrial articles afterwards. The MTO process flow primarily concerns a reaction unit, a product purifying unit and a product separating unit, wherein the reaction unit comprises a reactor and a regenerator, the product purifying unit comprises a quench tower, a water scrubbing tower, an alkaline washing tower and a drying tower, and the remaining part is the product separating unit. The reactor generally used in the MTO process is a fluid-bed reactor in which methanol, as the reactant, and olefins, as the products, are present in gas phase unexceptionally. The ratio of ethylene to propylene varies depending on the specific process applied. Current representative MTO arts include the processes developed by UOP, UOP/Hydro, Exxon Mobil and Dalian Chemical and Physical Research Institute of PRC. Along with the development of national economy and the growing demand on lower olefins, the starting materials of ethylene such as naphtha and light diesel oil are increasingly short of supply. Therefore, the concern of speeding up the industrial application of a MTO process has gained attention from various quarters.

In a MTO process, the product discharge stream that comes from the reactor and carries catalyst particles flows into a quench tower to be quenched. In the quench tower, water and methanol are condensed into liquids, while the product of olefins is still present in gaseous state. Since most of the catalyst particles will be captured by the quench water and get discharged from the quench tower, the quench water is rich in catalyst particles. In order to further remove the catalyst powder entrapped in the product gas stream, the gaseous olefin stream is fed into a water scrubbing tower to completely remove the catalyst via scrubbing. As a result, the catalyst powders are entrapped in the scrubbing water. Part of the quench water is cooled and then returns to the quench tower to be used as quench agent again, while the other part is fed into a stripping tower to separate methanol from water via stripping. The heat exchanger is so easily blocked by the large amount of catalyst particles in the quench water that the quench water must be purified. On the other hand, the catalyst particles in the stripping tower will deposit at the bottom of the tower, so that it is necessary to further remove the catalyst from the quench water before it enters the stripping tower in order to ensure the long-cycle operation of the stripping tower and reduce the pollution of downstream materials by the catalyst particles. If the catalyst in the scrubbing water is not removed, it will continuously accumulate, and therefore deteriorate the scrubbing efficiency as well as imperil the normal operation of the heat exchanger which is used to cool the scrubbing water before it is recycled.

U.S. Pat. No. 6,166,282 discloses a MTO fluid bed reactor, on top of which is equipped a set of cyclones to separate the solid catalyst particles from the product discharge stream, in order to prevent the catalyst particles from being carried out of the reactor. Despite the fact that the reaction gas stream flows through several cyclones, there are still catalyst particles which will exit the reactor along with the product discharge stream. These catalyst particles are separated from the gaseous product along with the quench water and the scrubbing water respectively in the quench tower and the scrubbing tower, and enter the water recycling system, leading to abrasion and clogging of the downstream equipments as well as the reduction of the operating cycle of the installation.

U.S. Pat. No. 5,744,680A discloses a method for preparing light hydrocarbons from oxides, wherein the stream comprising catalyst is expelled in a wet washing step. U.S. Pat. No. 6,870,072 also discloses that a wet washing section is used to remove the catalyst from the product discharge stream.

With respect to MTO quench water, U.S. Patent Application Publication No. 2005/0234281 A1 and Chinese Patent No. 1,942,558A disclose a combination of one or more solid-liquid cyclones or hydrocyclones operating in sequence or parallel for separating the catalyst which is recycled thereafter. The product stream has passed through several gas-solid cyclone separating units before it is discharged from the reactor, thus the catalyst particles in the MTO quench water have very small particle size (1-20 µm, wherein 80% of them have a particle size of less than 10 µm), with those in the scrubbing water even smaller (less than 5 µm). However, provided with an effective capture size in the range of 5-10 µm, a conventional solid-liquid cyclone or hydrocyclone can only be used to remove the catalyst particles lost under such abnormal conditions as that the solid-liquid cyclone does not function or the operation fails. In other words, solid particles smaller than 2 µm are hard or even impossible to be removed when the cyclone works normally. Thus, a conventional solid-liquid cyclone or hydrocyclone can only be used in an accident when catalyst particles are lost, whereas it can not fulfill the expected effect under normal operating conditions.

In addition, although one or more gas-solid separating devices are installed on top of a fluid bed reactor in prior art, a small amount of fine catalyst particles are still entrapped in the gaseous product stream exiting the reactor. The catalyst particles are expelled from the quench tower along with the reaction effluent and result in the containment of solid particles, which are hard to be removed, in the quench water to be stripped.

Therefore, taking into account the characteristics of the catalysts contained in the quench water and the scrubbing water of a MTO process as well as the operating conditions (i.e. the even distribution, small content and large throughput of the catalyst particles), it is highly desired in the art to develop a method for removing solid particles from MTO quench water and scrubbing water via mini-hydrocyclone separation under normal operating conditions.

SUMMARY OF THE INVENTION

According to the present invention, a novel method and a corresponding apparatus are provided for removing solids from MTO quench water and scrubbing water via mini-hydrocyclone separation, which overcomes the shortcomings in the prior art.

According to one aspect of the invention, a method is provided for removing solids from MTO quench water and scrubbing water via mini-hydrocyclone separation, comprising:

Removing the entrapped catalyst particles from the MTO quench water via mini-hydrocyclone separation;

Cooling the quench water purified via mini-hydrocyclone separation so as to effect the recycling of water;

Removing the entrapped catalyst particles from the MTO quench water to be stripped via mini-hydrocyclone separation, so as to reduce the deposition of the catalyst particles within the stripping tower;

Removing the entrapped catalyst particles from the MTO scrubbing water via mini-hydrocyclone separation; and Cooling the scrubbing water purified via mini-hydrocyclone separation so as to effect the recycling of water.

In one preferred embodiment, the operating temperature of the MTO quench water is 95-115° C., the content of the catalyst is 100-1000 mg/L, and the particle diameter of the catalyst is 1-20 μm.

In another preferred embodiment, the operating temperature of the MTO quench water to be stripped is 95-115° C., the content of the catalyst is 30-400 mg/L, and the particle diameter of the catalyst is 1-10 μm.

In still another preferred embodiment, the density of the MTO quench water and the MTO quench water to be stripped is 900-930 kg/m$^3$, the viscosity is 0.15-0.35 cp, and the density of the water-filled catalyst is 1300-1500 kg/m$^3$.

In yet another preferred embodiment, the operating temperature of the MTO scrubbing water is 30-50° C., the content of the catalyst is 70-800 mg/L, and the particle diameter of the catalyst is 1-10 μm.

In yet another preferred embodiment, the density of the MTO scrubbing water is 923-953 kg/m$^3$, and the viscosity is 0.551-0.751 cp.

In yet another preferred embodiment, after said mini-hydrocyclone separation is carried out, the content of the catalyst in the quench water decreases to less than 50 mg/L, and those in the quench water to be stripped and the scrubbing water decrease to less than 30 mg/L.

In yet another preferred embodiment, said mini-hydrocyclone separation is carried out using a mini-hydrocyclone separator.

In yet another preferred embodiment, said mini-hydrocyclone separator consists of a hydrocyclone core tube.

According to another aspect of the invention, an apparatus is provided for removing solids from MTO quench water and scrubbing water via mini-hydrocyclone separation, comprising:

A mini-hydrocyclone separator which is connected with a quench tower and used for removing the entrapped catalyst particles from the MTO quench water via mini-hydrocyclone separation; a quench water cooler which is connected with said mini-hydrocyclone separator and used for cooling the quench water purified via mini-hydrocyclone separation so as to effect the recycling of water; a scrubbing tower which is connected with said quench tower and used for scrubbing the product olefins separated in said quench tower to further remove the catalyst particles from the product olefins; a mini-hydrocyclone separator which is connected with said mini-hydrocyclone separator for the quench water and used for removing the entrapped catalyst particles from the MTO quench water to be stripped via mini-hydrocyclone separation; a stripping tower which is connected with said mini-hydrocyclone separator for the quench water to be stripped and used for separating methanol from water; a mini-hydrocyclone separator which is connected with said scrubbing tower and used for removing the entrapped catalyst particles from the MTO scrubbing water via mini-hydrocyclone separation; and a scrubbing water cooler which is connected with said mini-hydrocyclone separator and used for cooling the scrubbing water purified via mini-hydrocyclone separation so as to effect the recycling of water.

In one preferred embodiment, said mini-hydrocyclone separator consists of one, two or more hydrocyclone core tubes connected in parallel.

In another preferred embodiment, the flow rate of the water at the inlet of said mini-hydrocyclone separator for the quench water is 5-10 m/s, the pressure loss is 0.1-0.5 MPa, and the water inlet gauge pressure is 0.9-1.3 MPa.

In still another preferred embodiment, the flow rate of the water at the inlet of said mini-hydrocyclone separator for the quench water to be stripped is 8-15 m/s, the pressure loss is 0.2-0.5 MPa, and the water inlet gauge pressure is 0.7-1.0 MPa.

In yet another preferred embodiment, the flow rate of the water at the inlet of said mini-hydrocyclone separator for the scrubbing water is 8-15 m/s, the pressure loss is 0.1-0.3 MPa, and the water inlet gauge pressure is 1.2-1.6 MPa.

DETAILED DESCRIPTION OF THE INVENTION

After extensive and intensive study, the present inventors have found that the use of a hydrocyclone separator is the most effective and economical way for treating such solid-liquid systems as MTO quench water and scrubbing water which have high operating throughput and low content of solids. However, solid particles smaller than 5 μm are difficult to be removed under normal operating conditions due to the cut off diameter of a conventional hydrocyclone or hydrocyclone separator which is larger than 5 μm. Therefore, a method is invented for removing catalyst particles from quench water and scrubbing water via mini-hydrocyclone separation technology, since a mini-hydrocyclone separator has wide applicability, simple construction, strong adaptability, sound maintainability and high reliability, among other advantages, and more importantly, its separating efficiency ($d_{75}$<3 μm) is much higher than that of a common hydrocyclone separating apparatus. The invention is accomplished on the basis of the foregoing findings.

According to the reaction mechanism of MTO, at first, methanol is dehydrated to produce dimethyl ether, and then an equilibrium mixture of dimethyl ether and methanol is dehydrated to give lower olefins with ethylene and propylene being the main components, and a small amount of saturated hydrocarbons, aromatic hydrocarbons, etc., wherein a large quantity of water is produced by the dehydration reactions. After the product discharged stream is fed into a quench tower and cooled therein, catalyst particles are captured in the water. One part of the water is discharged from the bottom of the quench tower as so called bottom quench water, and the other part is discharged from the upper part of the quench tower. After cooling in the quench tower, the product olefins are scrubbed in a scrubbing tower to further remove the residual catalyst which is discharged thereafter from the bottom of the scrubbing tower along with water and thus entrapped in the scrubbing water. In normal operation, the content of catalyst in the product discharge stream is very low, and the particle size is very small. Therefore, the concentration of catalyst in both the quench water and the scrubbing water is quite low. However, owing to the density difference between catalyst and water, the solid catalyst particles in the quench tower do not distribute evenly along the axial direction, i.e. the closer to the bottom, the higher the catalyst concentration and the larger the particle size will be observed. Since the catalyst concentration in the quench water drawn off from the upper part of the quench tower is very low, the quench water can be sent to a cooler for cooling without solid-liquid separation and then recycled into the quench tower. When compared with the process in which all the quench water is discharged from the bottom of the tower, this process has the following advantages: 1. the workload and the running cost of the solid-liquid separating apparatus are reduced; 2. the solid content of the bottom water in the quench tower may be increased in favor of the solid-liquid separating efficiency. After passing a set of mini-hydrocyclone separators, one part of the purified bottom quench water is fed into a stripping tower for the separation of methanol via stripping, and the other part is recycled into the quench tower as quench agent. The purified scrubbing water after separation is also recycled into the scrubbing tower for reuse. On the other hand, two streams rich in catalyst are put into further treatment.

In order to ensure the safe operation of the stripping tower, the part of bottom quench water purified via mini-hydrocyclone separation is treated with a mini-hydrocyclone separator for quench water to be stripped to further remove catalyst particles before the bottom quench water enters the stripping tower. The purpose of stripping is to separate methanol from water. The resulting methanol is sent back to the reactor for reaction again, and water obtained is sent to another apparatus as a starting material for the production of synthetic gas in view of the effective use of water resource.

The catalyst in the quench water to be stripped has a low concentration (30-400 mg/L) and a small particle size (1-10 μm), but fine catalyst powder will still accumulate and affect the operation the stripping tower. In order to prolong the operating cycle of the stripping tower, the present inventors use a mini-hydrocyclone separator to purify the quench water to be stripped via mini-hydrocyclone separation. Said mini-hydrocyclone separator consists of several hydrocyclone core tubes and has the advantages of low operating pressure drop and energy consumption.

In the first aspect of the invention, a method is provided for enriching and recovering the solid catalyst contained in the quench water and the scrubbing water from a MTO process via a mini-hydrocyclone technique, comprising:

Discharging all the quench water from the bottom of the quench tower and performing the separation with a mini-hydrocyclone separator, after which one part of the water is sent into a mini-hydrocyclone separator for the quench water to be stripped, and the other part is cooled with a cooler before it is recycled into the quench tower as quench agent, wherein the mini-hydrocyclone separator is used to purify all the quench water;

Discharging one part of the quench water from the bottom of the quench tower, after which this part of quench water is treated via separation using a mini-hydrocyclone separator and cooled with a cooler before it is recycled into the quench tower as quench agent, and discharging the other part of the quench water from the middle to upper part of the tower, after which this part of water is sent into a mini-hydrocyclone separator for the quench water to be stripped, wherein the mini-hydrocyclone separator is only used to purify the quench water discharged from the bottom of the quench tower (the bottom quench water);

Discharging one part of the quench water from the bottom of the quench tower, after which this part of water is treated via separation using a mini-hydrocyclone separator and cooled with a cooler before it is recycled into the quench tower as quench agent, and discharging the other part of the quench water from the middle to upper part of the tower, after which this part of water is further divided into two parts, one part being sent into a mini-hydrocyclone separator for the quench water to be stripped, and the other part being cooled before it is recycled into the quench tower, wherein the mini-hydrocyclone separator is only used to purify the bottom quench water;

Removing the catalyst particles (i.e. those which are entrapped from the reactor and have a content of about 100-1000 mg/L, a density of about 900-930 kg/m$^3$, and a particle diameter of about 1-20 μm) from the bottom quench water/quench water originating from a MTO process via mini-hydrocyclone separation using a mini-hydrocyclone separator; and Removing the catalyst particles (which have a content of about 30-400 mg/L, a density of about 900-930 kg/m$^3$, and a particle diameter of about 1-10 μm) from the quench water to be stripped originating from a MTO process via mini-hydrocyclone separation using a mini-hydrocyclone separator; and Removing the catalyst particles (i.e. those which are entrapped from the reactor and have a content of about 70-800 mg/L, a density of about 923-953 kg/m$^3$, and a particle diameter of about 1-10 μm) from the bottom scrubbing water/scrubbing water originating from a MTO process via mini-hydrocyclone separation using a mini-hydrocyclone separator.

Preferably, the operating temperature of the quench water is about 95-115° C., the content of the catalyst is about 100-1000 mg/L, and the particle diameter of the catalyst is about 1-20 μm.

Preferably, the operating temperature of the quench water to be stripped is about 95-115° C., the content of the catalyst is about 30-400 mg/L, and the particle diameter of the catalyst is about 1-10 μm.

Preferably, the operating temperature of the scrubbing water is about 30-50° C., the content of the catalyst is about 70-800 mg/L, and the particle diameter of the catalyst is about 1-10 μm.

Preferably, the density of the quench water and the quench water to be stripped is about 900-930 kg/m$^3$, and the viscosity is about 0.15-0.35 cp.

Preferably, the density of the scrubbing water is about 923-953 kg/m³, and the viscosity is about 0.551-0.751 cp.

Preferably, the density of the water-filled catalyst in the quench water is about 1300-1500 kg/m³.

Figure 1:
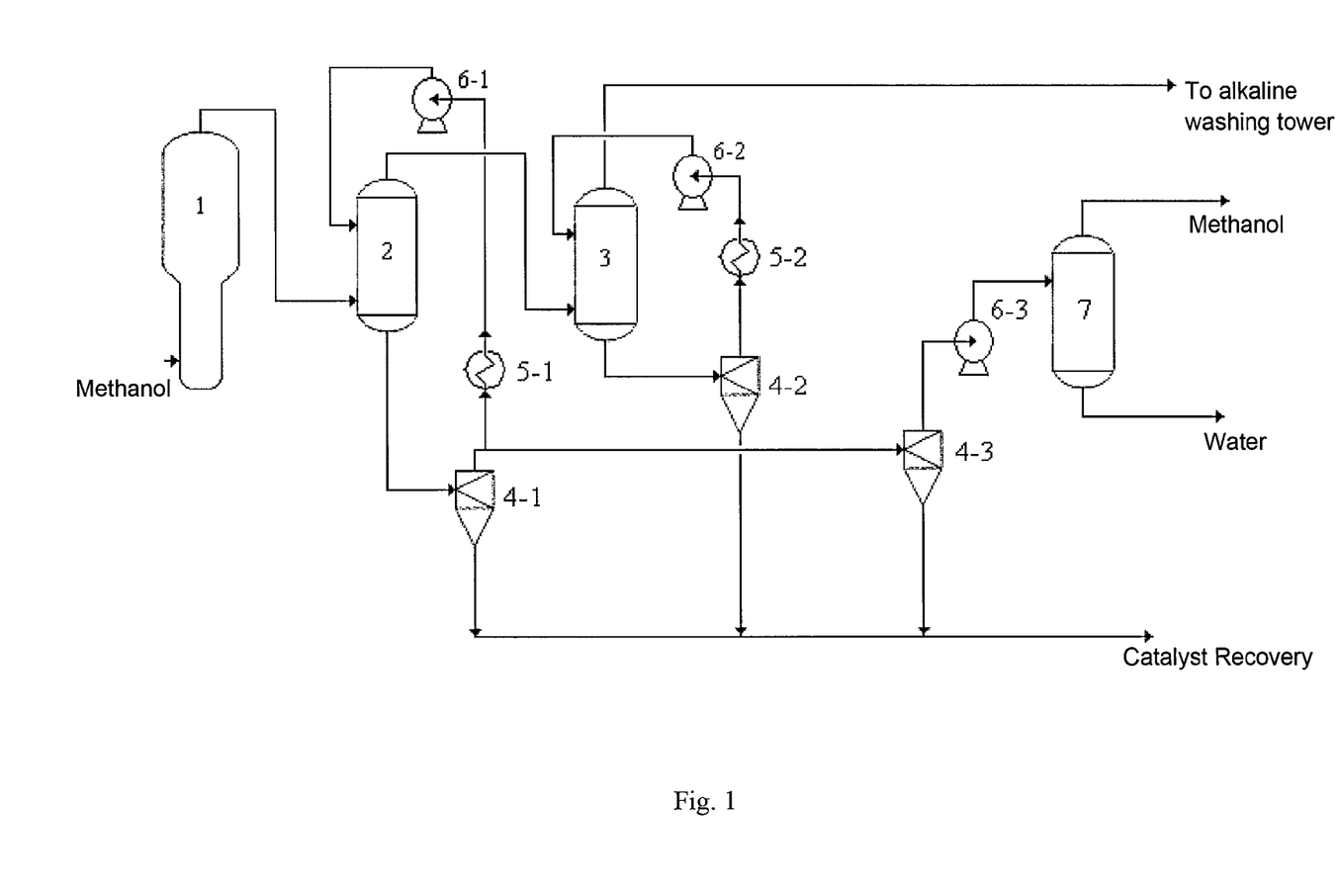
FIG. 1 is a schematic view showing a flow for purifying quench water and scrubbing water from a MTO process via mini-hydrocyclone separation in accordance with one embodiment of the present invention.

In the second aspect of the present invention, an apparatus is provided for enriching and recovering the solid catalyst contained in the quench water, quench water to be stripped and the scrubbing water from a MTO process via a mini-hydrocyclone technique, comprising:

A quench tower 2 which is connected with a MTO reactor 1 and used for quenching the product discharge stream carrying catalyst particles therein from the MTO reaction, so that water, methanol and catalyst are removed from olefins in the product, and methanol and most of the catalyst particles are captured in the quench water; a scrubbing tower 3 which is connected with said quench tower 2 and used for scrubbing the product of olefins separated in said quench tower 2, so as to further remove the residual catalyst particles from the product discharge stream; a mini-hydrocyclone separator 4-1 which is connected with said quench tower 2 and used for removing the solid catalyst particles from the bottom quench water via solid-liquid separation; a quench water cooler 5-1 which is connected with said mini-hydrocyclone separator 4-1 and used for cooling the quench water purified via the above solid-liquid separation so as to effect the recycling of water; a quench water pump 6-1 which is connected with said quench water cooler 5-1 and used for transferring the purified quench water cooled with said quench water cooler 5-1 to said quench tower 2; a mini-hydrocyclone separator 4-2 for the scrubbing water which is connected with said scrubbing tower 3 and used for removing the solid catalyst particles from the scrubbing water via solid-liquid separation, so as to remove the fine catalyst powder from the scrubbing water; a scrubbing water cooler 5-2 which is connected with said mini-hydrocyclone separator 4-2 for the scrubbing water and used for cooling the purified scrubbing water produced via separation; a scrubbing water pump 6-2 which is connected with said scrubbing water cooler 5-2 and used for transferring the purified scrubbing water cooled with said scrubbing water cooler 5-2 to said scrubbing tower 3, so as to effect a total recycle of water; and a mini-hydrocyclone separator 4-3 which is connected with said mini-hydrocyclone separator 4-1 for the quench water and used for performing solid-liquid separation to the quench water to be stripped, so as to remove the residual catalyst particles from the quench water to be stripped; a stripping water pump 6-3 which is connected with said mini-hydrocyclone separator 4-3 for the quench water to be stripped and used for transferring the purified quench water to be stripped to a stripping tower; a stripping tower 7 which is connected with said stripping water pump 6-3 and used for stripping the purified quench water to be stripped after said solid-liquid separation, so as to separate the unreacted methanol dissolved in the water.

Preferably, each set of said mini-hydrocyclone separators for the quench water, the quench water to be stripped and the scrubbing water consists of one or more mini-hydrocyclone separators.

Preferably, said mini-hydrocyclone separator consists of several sets of hydrocyclone core tubes.

Preferably, the flow rate of the water at the inlet of said mini-hydrocyclone separator for the quench water is about 5-10 m/s, the pressure loss is about 0.1-0.5 MPa, and the water inlet gauge pressure is about 0.9-1.3 MPa.

Preferably, the flow rate of the water at the inlet of said mini-hydrocyclone separator for the scrubbing water is about 8-15 m/s, the pressure loss is about 0.1-0.3 MPa, and the water inlet gauge pressure is about 1.2-1.6 MPa.

Preferably, the flow rate of the water at the inlet of said mini-hydrocyclone separator for the quench water to be stripped is about 8-15 m/s, the pressure loss is about 0.2-0.5 MPa, and the water inlet gauge pressure is about 0.8-1.1 MPa.

Preferably, the method and the apparatus according to the invention may also be used to purify the reaction effluent from a MTP (methanol to propylene) process or an OTO (oxide to light hydrocarbons) process.

Reference is now made to the drawings.

FIG. 1 is a schematic view showing a flow for purifying quench water and scrubbing water from a MTO process via mini-hydrocyclone separation in accordance with one embodiment of the invention. As shown in FIG. 1, after entering the MTO reactor 1 from its bottom, methanol undergoes a series of dehydration reactions at the presence of a catalyst to give olefins as the products which mainly comprise ethylene and propylene, and a large quantity of water is produced simultaneously. The products and the unconsumed reactant, all present in the MTO reactor 1 in gaseous state, exit from the top of the MTO reactor 1. The reaction products and part of the reactant from the MTO reactor 1 are fed to a quench tower 2 to be cooled therein, wherein the condensed water is discharged from the bottom of the quench tower 2 as the bottom quench water. Catalyst particles are removed from the bottom quench water with a mini-hydrocyclone separator 4-1 for the quench water, after which one part of the purified quench water is cooled with a quench water cooler 5-1 and then sent to the quench tower 2 via a quench water pump 6-1, while the other part of the purified quench water is sent to a mini-hydrocyclone separator 4-3 for the quench water to be stripped. The quenched reaction gas is then sent to a scrubbing tower 3 to be scrubbed, and the resulting reaction gas free of catalyst exits from the top of the scrubbing tower 3, whereas the water and the fine catalyst powder separated via scrubbing are discharged as a whole from the bottom of the scrubbing tower 3 to give so-called scrubbing water. The catalyst in scrubbing water is removed via a mini-hydrocyclone separator 4-2 for the scrubbing water and then the water is cooled with a scrubbing water cooler 5-2 before it is forced by a scrubbing water pump 6-2 to be recycled to the scrubbing tower 3. The purified quench water to be stripped is sent to a stripping tower via a stripping water pump 6-3 to separate methanol via stripping. The recovered methanol is recycled to the MTO reactor 1 to take part in the reaction again, while the resulting reaction water is used as a starting material for the production of synthetic gas.

Figure 2:
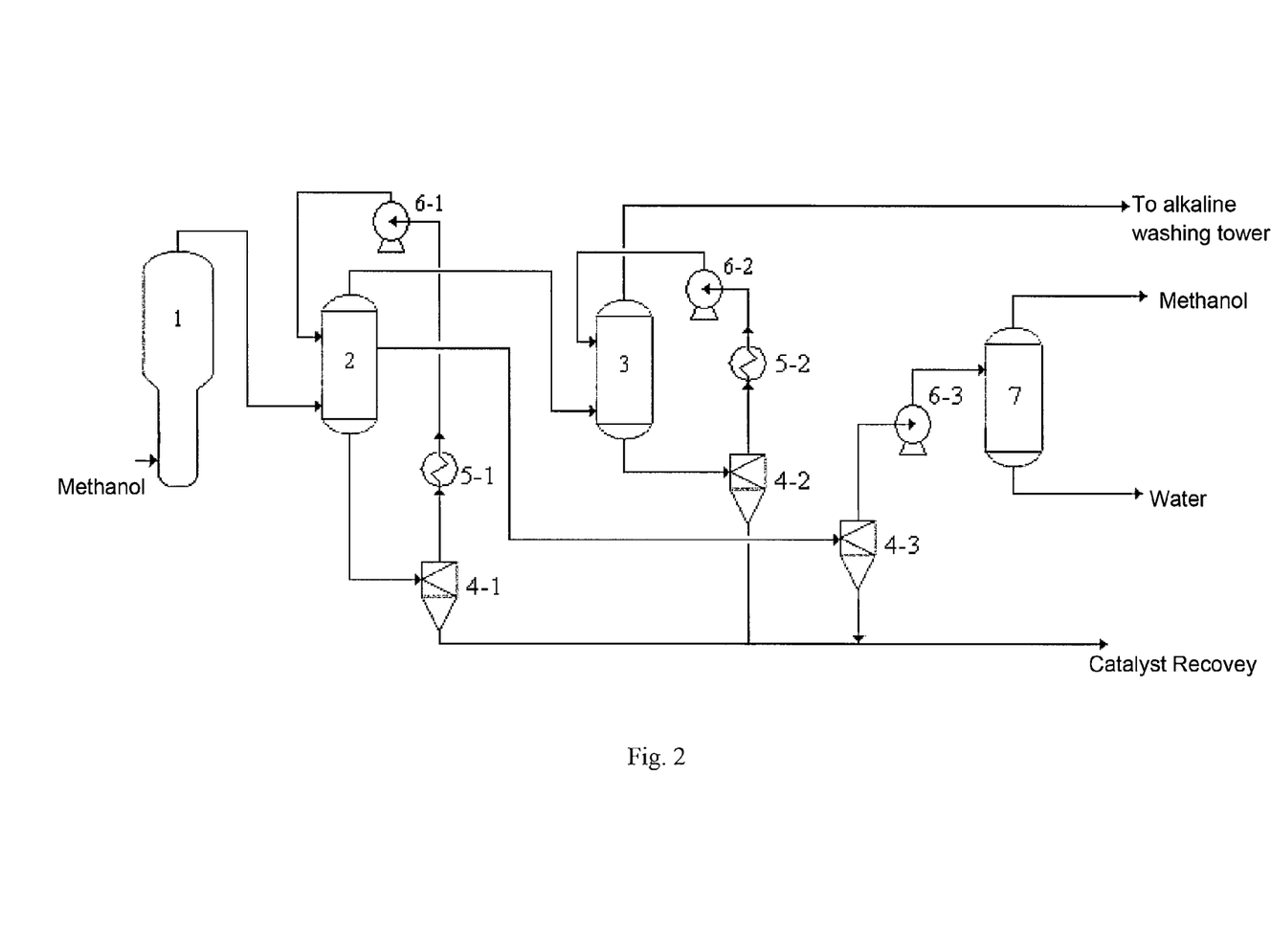
FIG. 2 is a schematic view showing a flow for purifying quench water and scrubbing water from a MTO process via mini-hydrocyclone separation in accordance with another embodiment of the present invention.

FIG. 2 is a schematic view showing a flow for purifying quench water and scrubbing water from a MTO process via mini-hydrocyclone separation in accordance with another embodiment of the invention. This flow is different from that shown in FIG. 1 in that solid-liquid mini-hydrocyclone separation is only performed to part of the quench water. A part of the quench water is discharged from the middle to upper part of the quench tower. For the higher the location is within the tower, the lower the content of the catalyst particles is thereat, when it is chosen to discharge the quench water from the upper part of the tower, this quench water may be sent directly to the mini-hydrocyclone separator for the quench water to be stripped.

As shown in FIG. 2, the reactants and the products are all present in gas state in the MTO reactor 1 from which the products and part of the unreacted reactant entrapping a small amount of catalyst particles exit during the reaction. The stream from the MTO reactor 1 is fed to a quench tower 2 to be cooled therein, producing condensed water which is called quench water. One part of the quench water is discharged from the bottom of the quench tower 2 as the bottom quench water. The other part of the quench water, which contains a very low content of catalyst, is discharged from the middle to upper part of the quench tower 2, and sent directly to a mini-hydrocyclone separator 4-3 for the quench water to be stripped. Catalyst particles are removed from the bottom quench water with a mini-hydrocyclone separator 4-1 for the quench water, after which the purified quench water is cooled with a quench water cooler 5-1 and then sent to the quench tower 2 via a quench water pump 6-1. The quenched reaction gas is then sent to a scrubbing tower 3 to be scrubbed, and the resulting reaction gas free of catalyst exits from the top of the scrubbing tower 3, whereas the water and the fine catalyst powder separated via scrubbing are discharged as a whole from the bottom of the scrubbing tower 3 to give so-called scrubbing water. The catalyst in the scrubbing water is removed via a mini-hydrocyclone separator 4-2 for the scrubbing water and then the scrubbing water is cooled with a scrubbing water cooler 5-2 before it is recycled to the scrubbing tower 3 via a scrubbing water pump 6-2. The purified quench water to be stripped is sent to a stripping tower via a stripping water pump 6-3 to separate methanol via stripping. The recovered methanol is recycled to the MTO reactor 1 to take part in the reaction again, while the resulting water is used as a starting material for the production of synthetic gas.

The catalyst particles in the quench tower are not evenly distributed, i.e. the higher the location is within the tower, the lower the content of the catalyst particles is thereat. Therefore, part of the quench water may be discharged from the middle to upper part of the tower, so as to reduce the workload of the mini-hydrocyclone separator for the quench water and hence the energy consumption for separation. Meanwhile, the concentration of the catalyst particles in the bottom quench water in FIG. 2 is higher than that in the flow shown in FIG. 1, thus the separating efficiency of the mini-hydrocyclone separator is higher for treating a stream of higher solid content.

Figure 3:
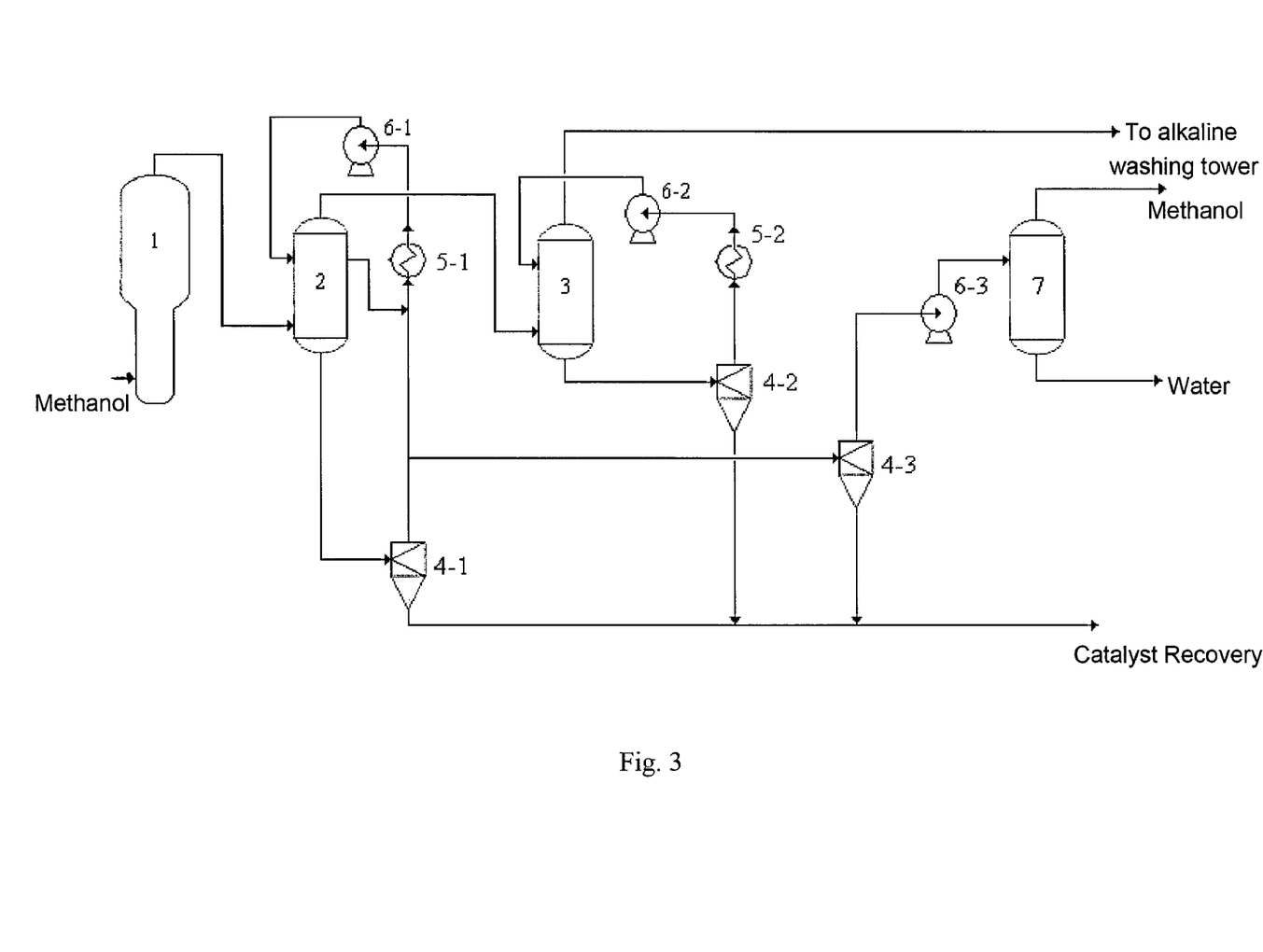
FIG. 3 is a schematic view showing a flow for purifying quench water and scrubbing water from a MTO process via mini-hydrocyclone separation in accordance with still another embodiment of the present invention.

FIG. 3 is a schematic view showing a flow for purifying quench water and scrubbing water from a MTO process via mini-hydrocyclone separation in accordance with still another embodiment of the invention. This flow is similar to that shown in FIG. 2 with the exception that less quench water is discharged from the bottom of the quench tower but more from the middle to upper part of the tower. The bottom quench water is transferred to a mini-hydrocyclone separator for the quench water for solid-liquid separation. One part of the other quench water is sent to a mini-hydrocyclone separator for the quench water to be stripped, and the other part is sent to a quench water cooler to be cooled before it is used as quench agent.

As shown in FIG. 3, the MTO reaction gas exiting from the MTO reactor 1 is fed to a quench tower 2 to be cooled therein. One part of the quench water that is condensed is discharged from the bottom of the quench tower 2 as the bottom quench water. The other part of the condensed water, which has a very low content of catalyst, is discharged from the middle to upper part of the quench tower 2. Subsequently, one part of it is directly transferred to a mini-hydrocyclone separator 4-3 for the quench water to be stripped, and the other part is combined with the purified quench water. The combined water is sent to a quench water cooler 5-1 to be cooled and then recycled into the quench tower 2 via a quench water pump 6-1. The quenched reaction gas is then sent to a scrubbing tower 3 to be scrubbed, and the resulting reaction gas free of catalyst exits from the top of the scrubbing tower 3, whereas the water and the fine catalyst powder separated via scrubbing are discharged as a whole from the bottom of the scrubbing tower 3 to give so-called scrubbing water. The catalyst in scrubbing water is removed via a mini-hydrocyclone separator 4-2 for the scrubbing water and then the scrubbing water is cooled with a scrubbing water cooler 5-2 before it is recycled to the scrubbing tower 3 via a scrubbing water pump 6-2. The purified quench water to be stripped is sent to a stripping tower via a stripping water pump 6-3 to separate methanol via stripping. The recovered methanol is recycled to the MTO reactor 1 to take part in the reaction again, while the resulting water is used as a starting material for the production of synthetic gas.

For less solid particles are contained in the quench water discharged from the upper part of the quench tower, it's desirable for the minimum quench water to be discharged from the bottom of the tower for the sake of saving energy. Recycling of the quench water to the quench tower without separation has the effect of enriching the catalyst particles in the tower. The solid content of the bottom quench water in the flow shown in FIG. 2 is lower than that in FIG. 3 but higher than that in FIG. 1. On the contrary, the energy consumption in the flow shown in FIG. 2 is lower than that in FIG. 1 but higher than that in FIG. 3. As high solid content favors the efficiency of hydrocyclone separation, the flow shown in FIG. 3 is the most preferred.

For the catalyst particles in the quench tower are not evenly distributed, i.e. the higher the location is within the tower, the lower the content of the catalyst particles is thereat, part of the quench water may be discharged from the middle to upper part of the tower, so as to reduce the workload of the mini-hydrocyclone separator for the quench water and therefore the energy consumption for separation. Meanwhile, the concentration of the catalyst particles in the bottom quench water in FIG. 3 is higher than that in the flow shown in FIG. 1, thus the separating efficiency of the mini-hydrocyclone separator is higher for treating a stream of higher solid content.

For less solid particles are contained in the quench water discharged from the upper part of the quench tower, it's desirable for the minimum quench water to be discharged from the bottom of the tower for the sake of saving energy. Recycling of the quench water to the quench tower without separation has the effect of enriching the catalyst particles in the tower. The solid content of the bottom quench water in the flow shown in FIG. 2 is lower than that in FIG. 3 but higher than that in FIG. 1. On the contrary, the energy consumption in the flow shown in FIG. 2 is lower than that in FIG. 1 but higher than that in FIG. 3. As high solid content favors the efficiency of hydrocyclone separation, the flow shown in FIG. 3 is the most preferred.

Some experimental data are listed in Table 1 below indicating the separating efficiency of a mini-hydrocyclone separator under various pressure loss.

TABLE 1

| Item | | Pressure loss/MPa | | | | |
|---|---|---|---|---|---|---|
| | | 0.20 | 0.25 | 0.30 | 0.35 | 0.40 |
| Concentration/ mg/L | Inlet | | | 218.44 | | |
| | Overflow | 60.32 | 55.91 | 58.17 | 38.10 | 29.89 |
| | Bottom flow | 1728.72 | 1818.24 | 1976.58 | 2032.54 | 2237.70 |
| | Separating Efficiency/% | 87.36 | 87.99 | 88.95 | 89.25 | 90.24 |

It can be seen from Table 1 above that by increasing the pressure loss, the separating efficiency can be improved, but the energy consumption of the process is increased similarly.

Therefore, the most preferable pressure loss of the mini-hydrocyclone separator is set in the range of 0.2-0.5 MPa in accordance to the invention.

The following Table 2 shows the size distribution of the fine catalyst particles in quench water to be stripped at the inlet and the overflow port when the pressure loss is 0.30 MPa and the concentration of the catalyst particles at the inlet is 218.44 mg/L.

TABLE 2

| Inlet | | Overflow | |
|---|---|---|---|
| Particle size (μm) | Volume below % | Particle size (μm) | Volume below % |
| 0.372 | 0.03 | 0.372 | 0.08 |
| 0.491 | 1.05 | 0.491 | 2.27 |
| 0.526 | 1.50 | 0.526 | 3.09 |
| 0.564 | 2.02 | 0.564 | 4.54 |
| 0.693 | 4.00 | 0.693 | 8.75 |
| 0.853 | 6.49 | 0.853 | 13.18 |
| 1.050 | 9.42 | 1.050 | 18.41 |
| 1.589 | 17.12 | 1.589 | 32.23 |
| 2.094 | 24.34 | 2.094 | 44.34 |
| 2.576 | 30.97 | 2.576 | 54.41 |
| 3.170 | 38.45 | 3.170 | 64.56 |
| 3.900 | 46.55 | 3.900 | 74.05 |
| 4.179 | 49.35 | 4.179 | 76.97 |
| 4.798 | 55.02 | 4.798 | 82.32 |
| 5.508 | 60.72 | 5.508 | 86.96 |
| 6.325 | 66.34 | 6.325 | 90.85 |
| 6.777 | 69.08 | 6.777 | 92.50 |
| 7.781 | 74.34 | 7.781 | 95.26 |
| 8.934 | 79.18 | 8.934 | 96.38 |
| 10.257 | 83.48 | 10.257 | 99.31 |
| 11.777 | 87.15 | 11.777 | 99.78 |
| 13.522 | 90.16 | 13.522 | 100.00 |
| 15.525 | 92.52 | 15.525 | 100.00 |
| 19.100 | 95.05 | 19.100 | 100.00 |
| 25.179 | 97.16 | 25.179 | 100.00 |
| 30.976 | 98.24 | 30.976 | 100.00 |
| 38.109 | 99.06 | 38.109 | 100.00 |
| 57.681 | 99.95 | 57.681 | 100.00 |

It can be seen from Table 2 above that 83.48% of the catalyst particles are smaller than 10.257 μm in size. Thus, it is difficult for a conventional hydrocyclone separator to achieve good separating efficiency. However, after mini-hydrocyclone separation, only 0.7% of the particles in the purified water at the outlet (overflow port) are larger than 10 μm in size, and the total separating efficiency is as high as 88.95%. Even for those particles having a particle size of 5.506 μm, the separating efficiency is about 80.0%.

The catalyst particles in the bottom quench water from the quench tower have a content of about 100-1000 mg/L, a density of about 1300-1500 kg/m$^3$ and a particle size of about 1-20 μm. The quench water containing a small amount of catalyst (operating pressure: about 0.9-1.3 MPa; operating temperature: about 95-115° C.) is fed into a mini-hydrocyclone separator at a flow rate of about 5-10 m/s and subjected to liquid-solid separation in a field of centrifugal force. The pressure loss (the pressure difference between the inlet and the outlet of the purified water) of the mini-hydrocyclone separator for the quench water is adjusted to be about 0.1-0.3 MPa. Owing to the large density difference between water and the catalyst particles, excellent separating effect is achieved, wherein the removal rate of the catalyst may be higher than about 80% by weight, and the $d_{75}$ cut off diameter of the particles may be smaller than about 5 μm.

The catalyst particles in the scrubbing water from the scrubbing tower has a content of about 70-800 mg/L and a particle size of about 1-10 μm. The quench water containing a small amount of catalyst (operating pressure: about 1.2-1.6 MPa; operating temperature: about 30-50□) is fed into a hydrocyclone separator at a flow rate of about 8-15 m/s and subjected to liquid-solid separation in a field of centrifugal force. When compared with the quench water, there is a larger proportion of small particles in the scrubbing water, so the pressure loss of the mini-hydrocyclone separator for the quench water is adjusted to be about 0.2-0.3 MPa, and the removal rate of the catalyst may also be higher than about 80% by weight, and the $d_{75}$ cut off diameter of the particles may be smaller than about 3 μm.

The catalyst particles in the quench water to be stripped produced from the mini-hydrocyclone separator for the quench water has a content of about 30-400 mg/L, a density of about 1300-1500 kg/m$^3$ and a particle size of about 1-20 μm. The quench water to be stripped containing a small amount of catalyst (operating pressure: about 0.8-1.1 MPa; operating temperature: about 95-115□) is fed into a hydrocyclone separator at a flow rate of about 8-15 m/s and subjected to liquid-solid separation in a field of centrifugal force. For the quench water to be stripped contains particles smaller in diameter than those in the quench water and has higher demand on separation, the pressure loss of the mini-hydrocyclone separator for the stripping water is adjusted to be about 0.2-0.5 MPa, and the removal rate of the catalyst in the quench water to be stripped may also be higher than about 80% by weight, and the $d_{75}$ cut off diameter of the particles may be smaller than about 3 μm.

The method and the apparatus according to the invention may also be used for removing oil drops or solid particles from other liquids.

The main advantages of the method and the apparatus according to the invention include:

Catalyst particles are removed from the quench water and the scrubbing water from a MTO process using a mini-hydrocyclone separator; the apparatus according to the invention is simple; high separating efficiency is achieved; the water is purified; the catalyst particles are recovered; and the operating cycles of the downstream equipments are prolonged.

All references mentioned in this disclosure are incorporated herein by reference, as if each of them would be incorporated herein by reference independently. In addition, it is to be appreciated that various changes or modifications can be made to the invention by those skilled in the art who have read the content taught above. These equivalents are intended to be included in the scope defined by the following claims of the application.

The invention claimed is:

1. An apparatus for removing catalyst particles from methanol-to-olefins MTO quench water and scrubbing water via mini-hydrocyclone separation, comprising:
   a mini-hydrocyclone separator which is connected with a quench tower and used for removing entrapped catalyst particles from the MTO quench water via mini-hydrocyclone separation;
   a quench water cooler which is connected with said mini-hydrocyclone separator and used for cooling the quench water purified via mini-hydrocyclone separation so as to effect the recycling of water;
   a scrubbing tower which is connected with said quench tower and used for scrubbing product olefins separated in said quench tower to further remove entrapped catalyst particles from the product olefins;
   a mini-hydrocyclone separator which is connected with said scrubbing tower and used for removing entrapped catalyst particles from the MTO scrubbing water via mini-hydrocyclone separation;

a scrubbing water cooler which is connected with said mini-hydrocyclone separator and used for cooling the scrubbing water purified via mini-hydrocyclone separation so as to effect the recycling of water;

a mini-hydrocyclone separator for the quench water to be stripped which is connected with said mini-hydrocyclone separator connected to said quench tower and is used for purifying the quench water to be stripped by removing trace amounts of entrapped catalyst particles from the quench water to be stripped; and a stripping water pump which is connected with said mini-hydrocyclone separator for the quenchwater to be stripped and used for transferring the purified quench water to be stripped to a stripping tower.

2. The apparatus of claim 1, wherein each of said mini-hydrocyclone separators consists of two or more hydrocyclone core tubes connected in parallel.

3. The apparatus of claim 2, wherein the flow rate at an inlet of each of said mini-hydrocyclone separators is 5-10 m/s, the pressure loss is 0.1-0.5 MPa, and the water inlet gauge pressure is 0.9-1.3 MPa.

4. The apparatus of claim 2, wherein the flow rate at an inlet of each of said mini-hydrocyclone separators is 8-15 m/s, the pressure loss is 0.1-0.3 MPa, and the water inlet gauge pressure is 1.2-1.6 MPa.

5. The apparatus of claim 2, wherein the flow rate at an inlet of each of said mini-hydrocyclone separators is 8-15 m/s, the pressure loss is 0.2-0.5 MPa, and the water inlet gauge pressure is 0.8-1.1 MPa.

6. The apparatus of claim 1, wherein the flow rate at an inlet of each of said mini-hydrocyclone separators is 5-10 m/s, the pressure loss is 0.1-0.5 MPa, and the water inlet gauge pressure is 0.9-1.3 MPa.

7. The apparatus of claim 1, wherein the flow rate at an inlet of each of said mini-hydrocyclone separators is 8-15 m/s, the pressure loss is 0.1-0.3 MPa, and the water inlet gauge pressure is 1.2-1.6 MPa.

8. The apparatus of claim 1, wherein the flow rate at an inlet of each of said mini-hydrocyclone separators is 8-15 m/s, the pressure loss is 0.2-0.5 MPa, and the water inlet gauge pressure is 0.8-1.1 MPa.

9. A method for removing catalyst particles from methanol-to-olefins (MTO) quench water and scrubbing water using the apparatus recited in claim 8, comprising:

removing entrapped catalyst particles from the MTO quench water via mini-hydrocyclone separation using the mini-hydrocyclone separator which is connected with the quench tower;

cooling the quench water purified via mini-hydrocyclone separation so as to effect the recycling of water using the quench water cooler;

removing entrapped catalyst particles from the MTO quench water to be stripped via mini-hydrocyclone separation using the mini-hydrocyclone separator which is connected to the scrubbing tower, so as to reduce the deposition of catalyst particles within the stripping tower;

removing entrapped catalyst particles from the MTO scrubbing water via mini-hydrocyclone separation using the mini-hydrocyclone separator which is connected to the quench tower; and cooling the scrubbing water purified via mini-hydrocyclone separation using the quench water cooler so as to effect the recycling of water.

10. The method of claim 9, wherein an operating temperature of the MTO quench water is 95-115° C., a content of entrapped catalyst particles is 100-1000 mg/L, and a particle diameter of entrapped catalyst particles is 1-20 μm.

11. The method of claim 10, wherein the density of the MTO quench water and the MTO quench water to be stripped is 900-930 kg/m$^3$, and the viscosity is 0.15-0.35 cp.

12. The method of claim 9, wherein an operating temperature of the MTO quench water to be stripped is 95-115° C., a content of entrapped catalyst particles is 30-400 mg/L, and a particle diameter of entrapped catalyst particles is 1-10 μm.

13. The method of claim 12, wherein the content of the entrapped catalyst particles is reduced to less than 30 mg/L after said mini-hydrocyclone separation.

14. The method of claim 12, wherein the density of the MTO quench water and the MTO quench water to be stripped is 900-930 kg/m$^3$, and the viscosity is 0.15-0.35 cp.

15. The method of claim 9, wherein the density of the MTO quench water and the MTO quench water to be stripped is 900-930 kg/m$^3$, and the viscosity is 0.15-0.35 cp.

16. The method of claim 9, wherein an operating temperature of the MTO scrubbing water is 30-50° C., a content of entrapped catalyst particles is 70-800 mg/L, and a particle diameter of entrapped catalyst particles is 1-10 μm.

17. The method of claim 16, wherein the density of the MTO scrubbing water is 923-953 kg/m$^3$, and the viscosity is 0.551-0.751 cp.

18. The method of claim 16, wherein the content of the entrapped catalyst particles is reduced to less than 30 mg/L after said mini-hydrocyclone separation.

19. The method of claim 9, wherein the density of the MTO scrubbing water is 923-953 kg/m$^3$, and the viscosity is 0.551-0.751 cp.

* * * * *